(12) United States Patent
Henke et al.

(10) Patent No.: US 6,431,006 B1
(45) Date of Patent: Aug. 13, 2002

(54) SOIL TESTING ASSEMBLIES

(75) Inventors: Robert Henke; Wanda Henke, both of Lutherville, MD (US)

(73) Assignee: Dynamic In Situ Geotechnical Testing Incorporated, Lutherville, MD (US)

( * ) Notice: Subject to any disclaimer, the term of this patent is extended or adjusted under 35 U.S.C. 154(b) by 0 days.

(21) Appl. No.: 09/423,128

(22) PCT Filed: Jun. 4, 1998

(86) PCT No.: PCT/US98/11643

§ 371 (c)(1),
(2), (4) Date: Nov. 5, 1999

(87) PCT Pub. No.: WO98/57143

PCT Pub. Date: Dec. 17, 1998

Related U.S. Application Data

(60) Provisional application No. 60/049,341, filed on Jun. 11, 1997, provisional application No. 60/059,463, filed on Sep. 22, 1997, and provisional application No. 60/081,917, filed on Apr. 16, 1998.

(51) Int. Cl.⁷ ........................... G01N 3/22; G01N 33/24; G01N 3/24
(52) U.S. Cl. ............................ 73/784; 73/843; 73/847
(58) Field of Search ........................... 73/84, 843, 847, 73/784, 841, 866

(56) References Cited

U.S. PATENT DOCUMENTS

| | | | |
|---|---|---|---|
| 3,709,031 A | | 1/1973 | Wilson et al. ............ 73/84 X |
| 3,712,121 A | | 1/1973 | Fletcher et al. .............. 73/84 |
| 3,797,301 A | | 3/1974 | Hawes ...................... 73/84 |
| 4,302,967 A | | 12/1981 | Dufey ....................... 73/84 |
| 4,594,899 A | * | 6/1986 | Henke et al. .............. 73/784 |
| 5,203,824 A | * | 4/1993 | Henke et al. .......... 73/864.43 |
| 5,931,237 A | * | 8/1999 | Henke et al. ........... 73/84 X |

FOREIGN PATENT DOCUMENTS

| | | | |
|---|---|---|---|
| DE | 3 905409 A1 | * 8/1990 | .................. 73/84 |
| DE | 4328540 A1 | * 1/1994 | ................ 73/841 |

(List continued on next page.)

OTHER PUBLICATIONS

Derwent abstract SU 499517A "Rotational Sheer Soil tester—with hydraulic cylinder compressing gas and second turning sheering by rack and pinion" Assignee Power Syst Elec Net, Mar. 1976.*

Derwent abstract of SU 653553 A "Shear torque firmness testing—by rotating blades and cylindrical cover together with, and separate from, specific torque measurement in each case" Chernikov et al, Mar. 1979.*

Derwent abstract of SU 873018 B Solid Sheer strength test tool—with concave half–cylindrical blades on shank Chernikov et al, Oct. 1981.*

Derwent abstract of SU 1154586 A "Solid Sheer strength test stand—uses recording device with hydraulic cylinder with spring–loaded upright" Assignee Energosetproekt, May 1985.*

Dynamic In Situ Geotechnical Testing, Inc. Report prepared thereby for the U.S. National Science Foundation and the U.S. Federal Highway Administration, In Situ Nonlinear Shear Stress vs Strain Characteristics for Shallow Layers of Soil: 1–10/La Cienega Blvd., Undercrossing, Los Angeles, California, Appendix A: Simplified Torsional Cylindrial ImpulseShear Test, Prototype Testing Systems, and General Procedures. Nov. 1996. pp. A1–A5, especially: p. A1, A3 and A4 and p. A5, lines 1–7.

*Primary Examiner*—Thomas P. Noland
(74) *Attorney, Agent, or Firm*—Trop, Pruner & Hu, P.C.

(57) ABSTRACT

A single open ended testing cylinder which is attached to wireline probe instrumented head is positioned at the lower end of a conventional hollow-stem drilling auger which is penetrated into the soil therebelow. During testing cylinder is rotated in the soil while torsional loading is measured and axial loading bypassed.

10 Claims, 9 Drawing Sheets

FOREIGN PATENT DOCUMENTS

| | | | | |
|---|---|---|---|---|
| EP | 64753 A1 | * 11/1982 | ................ | 73/775 |
| JP | 56-142913 | * 11/1981 | ................ | 73/84 |
| JP | 58-71432 | * 4/1983 | ................ | 73/818 |
| JP | 59-52730 A | 3/1984 | ................ | 73/800 |
| JP | 60-73432 A | 4/1985 | ................ | 73/826 |
| JP | 8-285747 | * 11/1996 | ............ | G01N/3/24 |

* cited by examiner

SOIL TESTING ASSEMBLIES

CROSS REFERENCE TO RELATED APPLICATIONS

This application is based on Provisional Application No. 60/049,341, filed Jun. 11, 1997, No. 60/059,463, filed Sep. 22, 1997 and No. 60/081,917 filed Apr. 16, 1998, and claims the benefit thereof.

FIELD OF THE INVENTION

This invention relates generally to techniques for testing soil.

BACKGROUND OF THE INVENTION

It is often important to determine properties such as the resistance of soil to liquefaction, the degradation characteristics of soil, the shear modulus of soil at low levels of shear deformation, and the variation in shear modulus of soil with shear deformation. Commonly, these soil properties, as well as others, are necessary for analyses which predict the response of a site or foundation structure system to dynamic loading caused by earthquakes, ocean waves, or mechanical vibrations.

Soil properties may be determined by in situ field tests. For example, the liquefaction resistance of the soil may be determined by penetration tests that involve penetrating a closed-ended probe into the ground at a slow, controlled rate or driving a cylinder into the ground by violent impacts. The resistance of the soil to liquefaction is correlated to the resistance of the probe or cylinder during penetration.

A technique that can measure the resistance to liquefaction by torsionally exciting the soil is disclosed in U.S. Pat. Nos. 4,594,899 and 5,203,824 to Robert and Wanda Henke. In these patents, the illustrated testing device includes a pair of concentric open-ended cylinders that are inserted into the soil to be tested. A torque may be applied to the inner cylinder and the response of the cylinder in the soil to the applied torque may be measured by sensors mounted on the inner cylinder.

In such soil tests, a borehole is drilled to access a soil sample and the testing device is lowered down the borehole to test the soil. The testing device may be secured to an auger in the borehole. The testing device may be subjected to substantial applied forces or torques or other reaction forces from the soil. Thus, the auger to which the testing device is anchored may serve as a reaction means to carry out various operations on the testing device.

SUMMARY OF THE INVENTION

A soil testing assembly includes a soil testing cylinder and a housing. An extractor rod connects the testing cylinder and the housing while allowing relative axial movement between the rod, the housing and the testing cylinder.

BRIEF DESCRIPTION OF THE DRAWINGS

FIG. 1A is a graph of applied torque versus time;

FIG. 1B is a graph of probe rotational response versus time;

DESCRIPTION OF THE PREFERRED EMBODIMENTS

Figure 1:
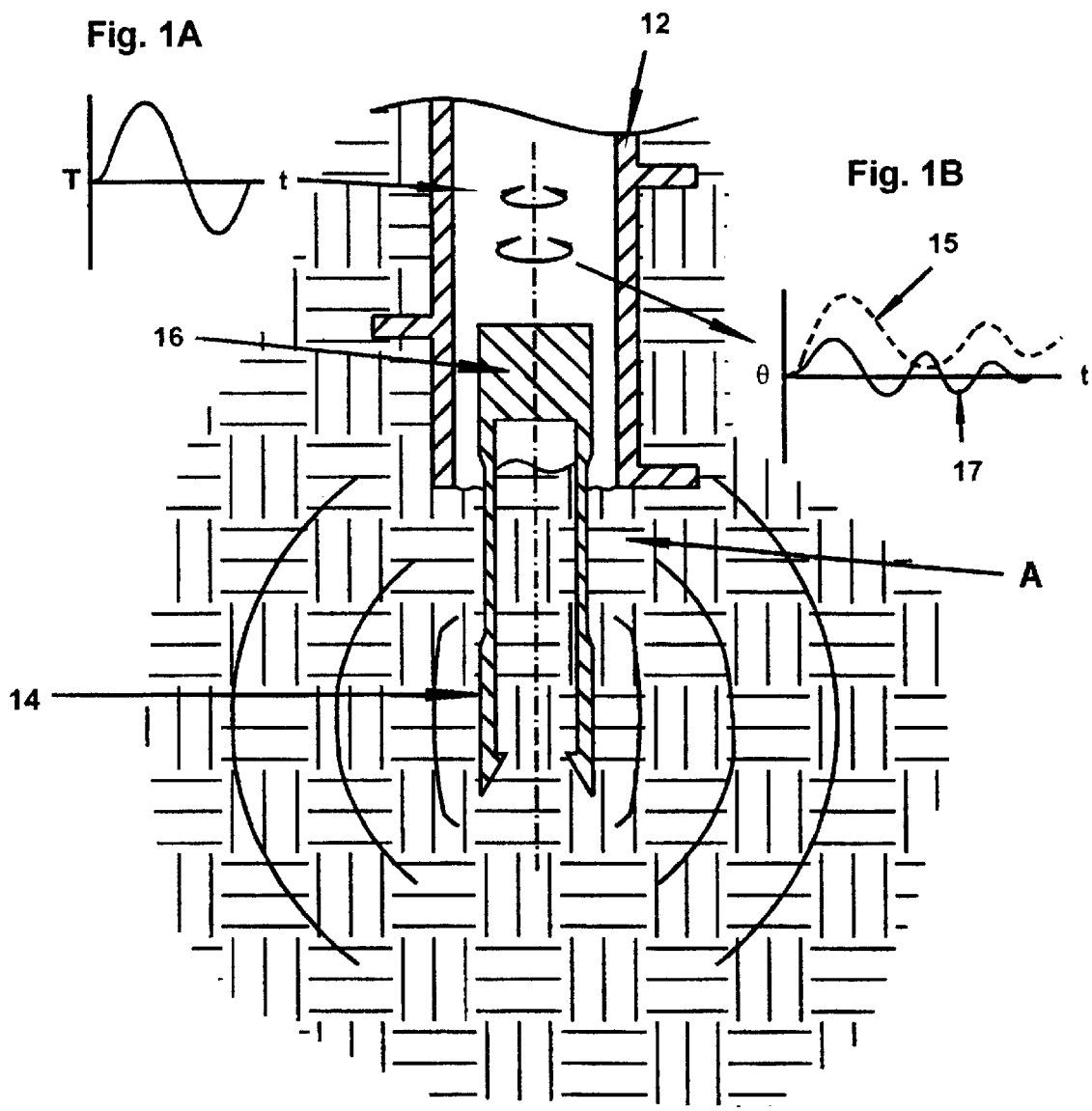
FIG. 1 is a schematic depiction of key elements of a single cylinder probe in use.

Referring to FIG. 1, a single cylinder 14 attached to the instrumented head 16 of a wireline probe, positioned at the lower end of a conventional hollow-stem drilling auger 12, is penetrated into the soil "A" below the auger. The test soil surrounds the lower portion of the open ended testing cylinder 14. To conduct a test, an impulsive torque T (FIG. 1A) of a selected level is applied over time t through an instrumented head 16, to the cylinder 14 to induce shear stresses and strains in the test soil A. The instrumented head 16 and the cylinder 14 respond by vibrating rotationally at an angle θ over time t in a manner that appears to be strongly dependent on shear moduli and related deformation parameters of the test soil as indicated in FIG. 1B. Shear moduli and the related parameters are inferred from torque and rotation measurement by simulating tests analytically. The stiff soil response 17 maybe compared to the soft soil response 15 in FIG. 1B.

Figure 2:
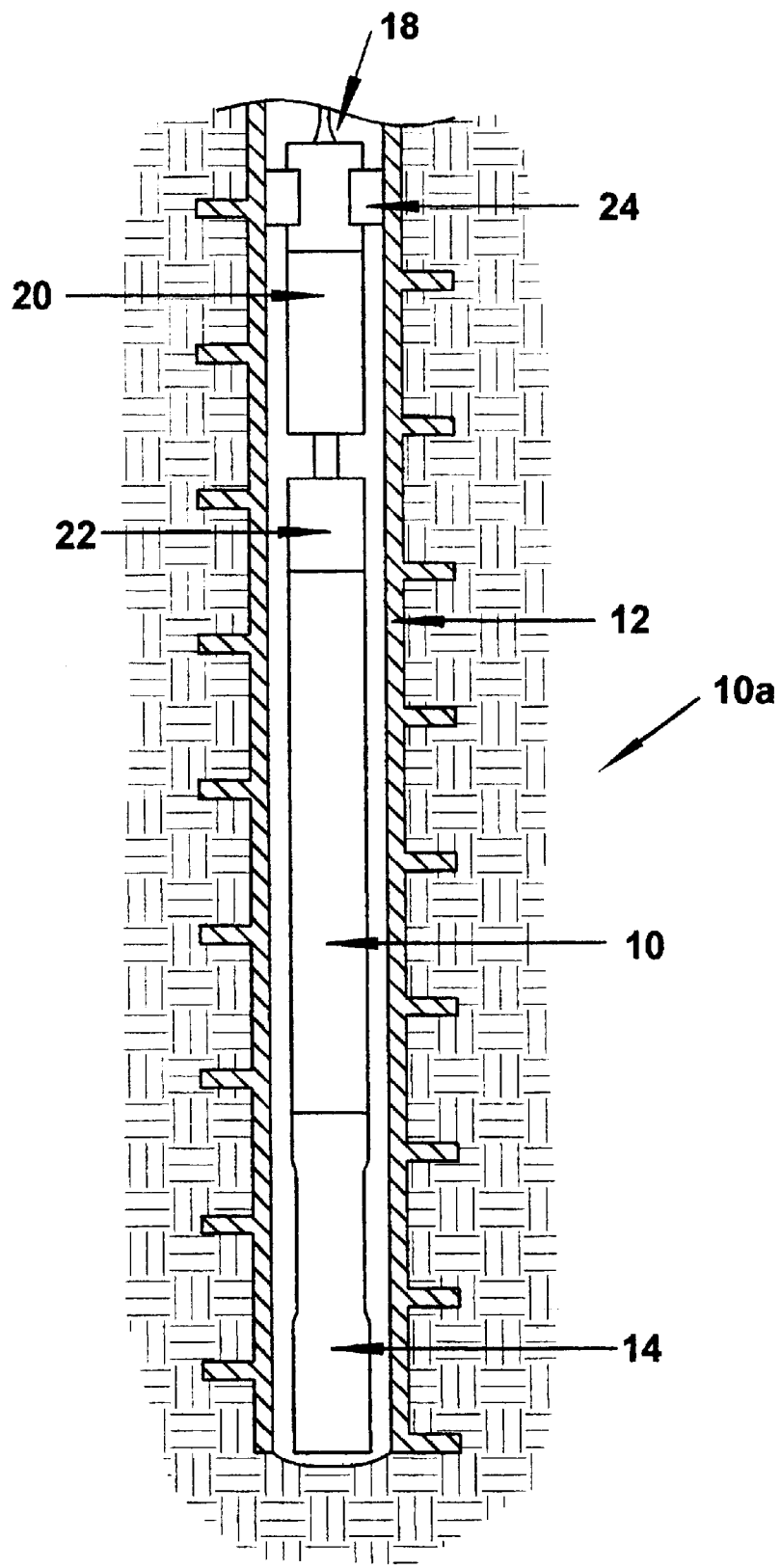
FIG. 2 is a cross-sectional view of an embedded auger assembly to which a probe has been clamped.

Referring to FIG. 2, a probe 10 in a single cylinder torsional cylindrical shear testing system 18 is clamped into an auger assembly 12 prior to penetration of the probe cylinder 14 into the soil to be tested. The probe may include a penetration cylinder 20 and an axial load cell 22 as well as lateral clamps 24 to clamp the probe 10 inside the auger assembly 12.

Figure 3:
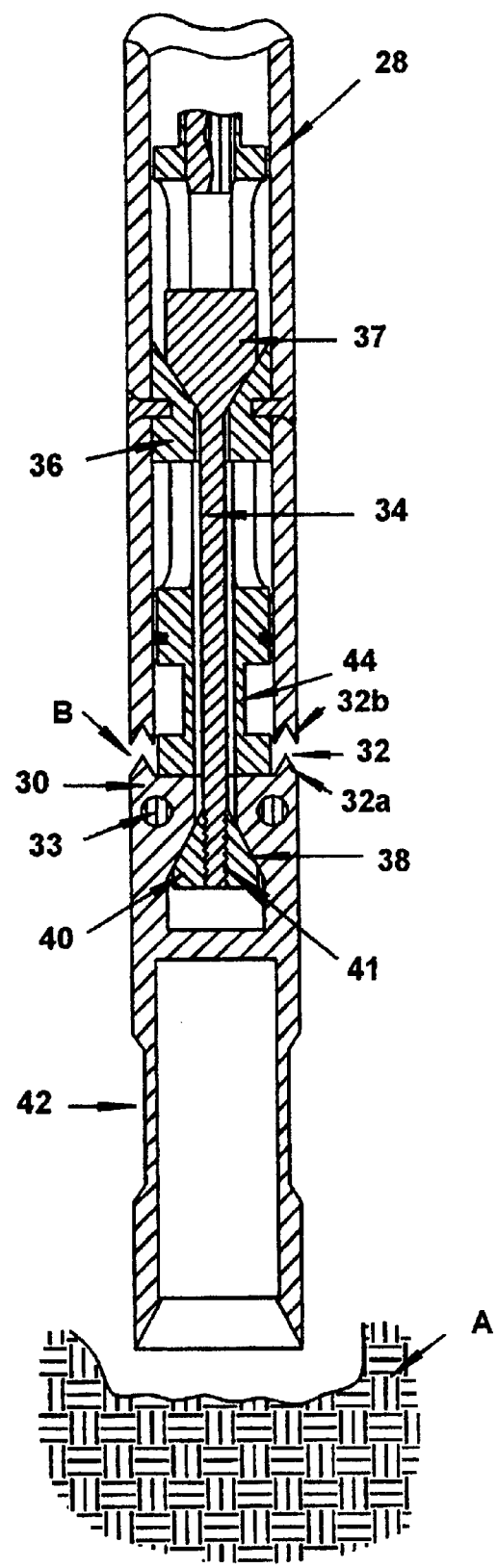
FIG. 3 is a cross-sectional view of the lower portion of the probe in a first position.

The lower portion 10a of the probe 10, shown in FIG. 3, includes a housing 28, an instrumented head 30 and a probe cylinder 42 that may be partially separated from one another at B. The junction 32 between the housing and the instrumented head/probe cylinder assembly allows axial displacement between the two units but through friction, resists relative rotation when the two units are in full engagement. A cylinder extractor rod 34 communicates between the probe housing 28 and the instrumented head 30. A collar 36 for the enlarged head 37 provides engagement between the cylinder extractor rod 34 and the probe housing 28 and a seat 38 for the enlarged foot 40 of the cylinder extractor rod 34 provides engagement between the cylinder extractor rod 34 and the instrumented head 30. A v-shaped annular groove 32b is formed in the housing 28 to mate well with the v-shaped ring 32a on the instrumented head 30. The groove 32b and ring 32a help align the mating pieces.

Initially, as shown in FIG. 3, the instrumented head 30 and the probe cylinder 42 are suspended by the cylinder extractor rod 34 above the soil A. The separation of the junction 32 between the housing and the instrumented head and probe cylinder assembly is at its maximum. The separation is limited by the cylinder extractor rod assembly and the collar 36 and seat 38 against which the head 37 and foot 40 bear. The head and foot of the cylinder extractor rod 34 and the corresponding facing surfaces are configured so that the housing and instrumented head 30/probe cylinder 42 assembly are not separated by more than the distance existing when the head 37 of the cylinder extractor rod bears against the collar 36 and the foot 40 of the cylinder extractor rod 34 bears against the seat 38. The conical shapes of the foot 40 and head 37 of the cylinder extractor rod and the corresponding bearing surfaces 36, 38 contribute toward proper alignment between the housing and the instrumented head/probe cylinder assembly. The foot 40 may be connected to the rod 34 by threads 41. An accelerometer 33 is provided as well.

Figure 4:
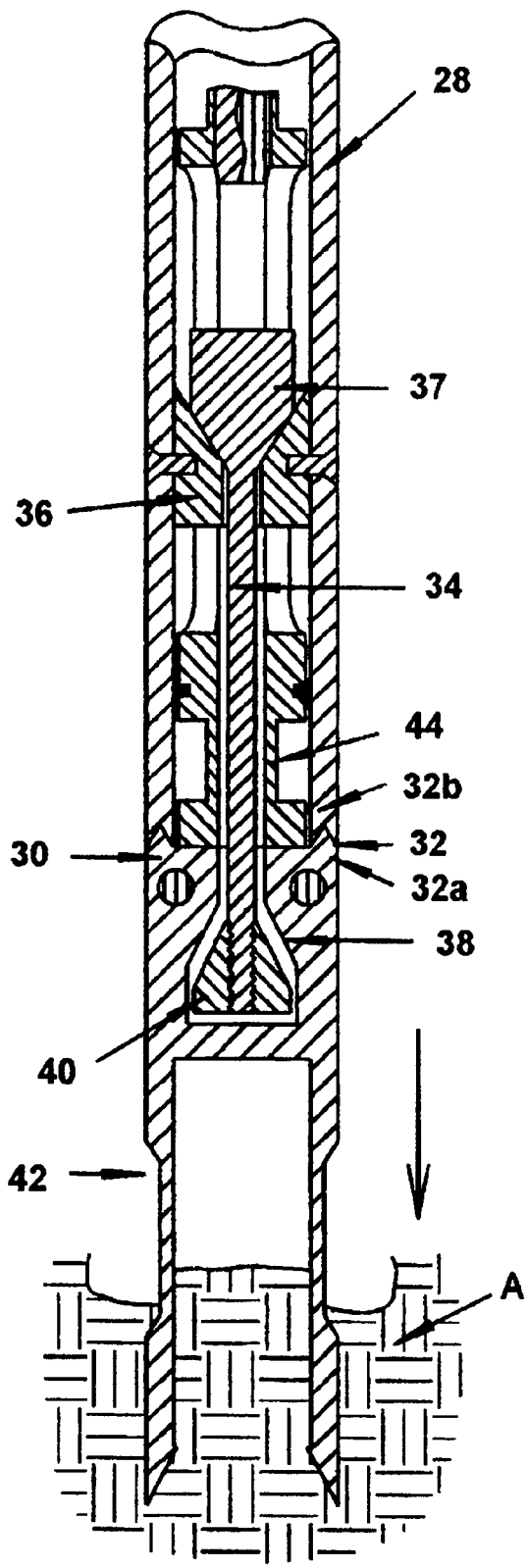
FIG. 4 is a cross-sectional view of the lower portion of the probe in a second position.

As shown in FIG. 4, the probe cylinder 42 is penetrated, in the direction indicated, into the soil A to be tested by the penetration cylinder. The reaction force needed to penetrate the probe cylinder is derived from an auger assembly to which the probe is clamped (FIG. 2). The probe is in a compressed state in FIG. 4, with the housing 28 and the instrumented head 30/probe cylinder 42 assembly in contact with each other at the junction 32.

During penetration, the compressive force acting within the probe is transmitted through the penetration cylinder to the instrumented head 30/probe cylinder 42 assembly through the housing. Compressive force is not transmitted through the torsional load cell 44. This is very desirable because the compressive force developed during penetration may be quite large. While the wall of the housing may be robust and readily able to withstand such force, the torsional load cell 44 is generally thin-walled in order to measure low levels of torque. The load cell could collapse under modest compressive force. With the probe in the compressed state the cylinder extractor rod 34 is freely suspended from the cylinder extractor rod collar 36. The separation between the foot 40 of the cylinder extractor rod and the seat 38 for the foot is at its maximum.

Figure 5:
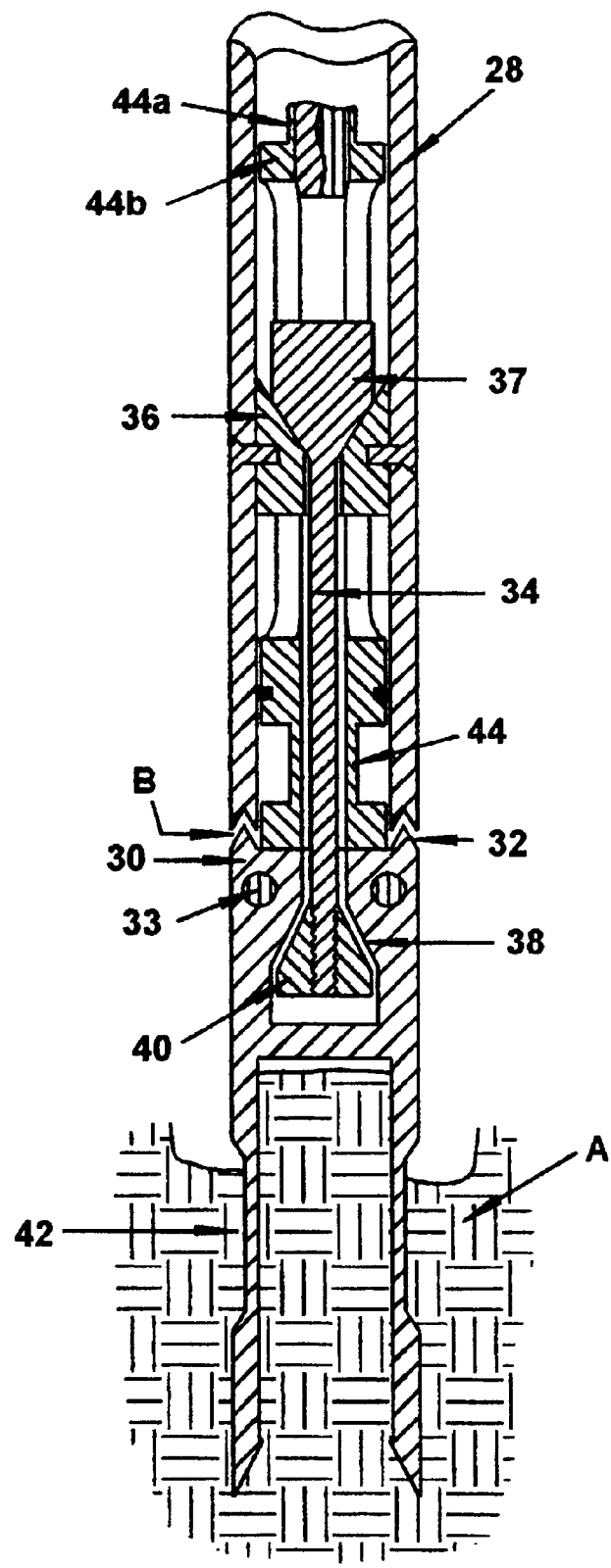
FIG. 5 is a cross-sectional view of the lower portion of the probe in a third position.

In the next stage, shown in FIG. 5, the probe cylinder 42 has been fully penetrated into the soil, the penetration force has been relieved, and the probe is ready for testing. The probe is in a partially extended state in which the housing 28 has been raised (using the penetration cylinder, for example,) from the instrumented head 30/probe cylinder 42 assembly by an intermediate amount; that is, there is a gap B of selected size at the junction 32 between the housing and the instrumented head 30/probe cylinder 42 assembly. In this state, during a test, all the torque applied to the instrumented head 30/probe cylinder 42 assembly passes through the torsional load cell 44 without passing through the housing 28. The load cell 44 is secured to the instrumented head 30 by screws. If some of the applied torque passed to the instrumented head 30/probe cylinder 42 assembly through the housing, this torque would not have been measured and the torque measured by the torsional load cell would not have represented the full torque applied to the instrumented head 30/probe cylinder 42 assembly. This could create uncertainty in the interpretation of test results, since the torsional excitation would not be fully defined.

Additionally, with the instrumented head 30/probe cylinder 42 assembly separated from the housing 28, this assembly would be able to rotate freely during a test. Under this condition, the test soil would be expected to have the greatest impact on the rotational response of the instrumented head 30/probe cylinder 42 assembly and thus, this response would reflect the relevant characteristics of the soil being tested to the greatest possible extent. In contrast, if the instrumented head 30/probe cylinder 42 assembly were restrained as a result of the contact between the housing 28 and the instrument head 30 the impact of the test soil on the rotational response of this assembly would be lessened by an unknown amount. The response of the assembly would not reflect the relevant characteristics of the soil being tested to the same degree as in the case for which the housing and the instrumented head 30/probe cylinder 42 assembly are separated. Thus, the desired soil characteristics would not be easy to infer from test results as in the latter case. With the probe in the partially extended state, the cylinder extractor rod 34 is freely suspended from the cylinder extractor rod collar 36 and the separation between the foot 40 of the cylinder extractor rod and the seat 38 for this foot is of an intermediate amount.

The test is conducted by a motor drive (not shown) connected to the keyed end 44a of an extension 44b of the load cell 44. A torque is applied to the instrumented head 30/probe cylinder 42 assembly through the load cell 44 and the rotary response of the instrumented head 30/probe cylinder 42 assembly is then detected by the accelerometer 33.

Figure 6:
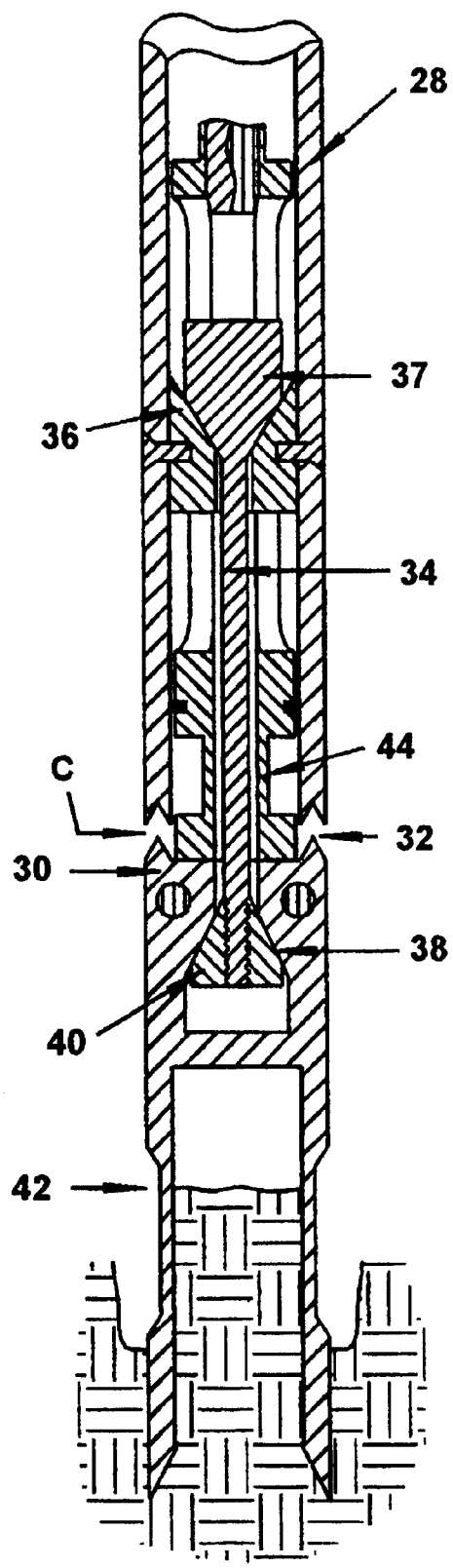
FIG. 6 a cross-sectional view of the lower portion of the probe in a fourth position.

In the next stage, shown in FIG. 6, the probe cylinder 42 is being extracted from the test soil by the penetration cylinder 20 (FIG. 2). The probe is in the fully extended state as it was during the first stage (FIG. 3) and the housing 28 and the instrumented head 30/probe cylinder 42 assembly are separated from each other by the greatest possible amount as indicated at C. However, in this stage, because of the resistance exerted by the soil on the probe cylinder 42, the cylinder extractor rod 34 is under considerable tension. This tension force does not pass through the torsional load cell 44. Thus, the torsional load cell 44 is protected from damage during extraction (as well as the penetration of the probe cylinder). As in the first stage (FIG. 3), with the probe in the fully extended state, the head 37 of the cylinder extractor rod 34 bears against the collar 36 for the cylinder extractor rod and the foot 40 of the cylinder extractor rod 34 bears against the seat 38 for this foot. Again, the conical shapes of the head 37 and foot 40 of the cylinder extractor rod 34 and the corresponding bearing surfaces contribute to proper alignment between the housing 28 and the instrumented head 30/probe cylinder 42 assembly.

It is also possible that the opening and closing of the junction 32 between the housing 28 and the instrumented head 30/probe cylinder 42 assembly could be monitored using a position measuring sensor, an electrical switch, or an axial load cell that measures the force within the probe along the longitudinal axis of the probe. Also, the region of the probe enclosed by the housing could be pressurized. This could be of value, for example, when conducting tests with the probe submerged at depth underwater. The internal pressure could lessen some of the adverse effects of large external fluid pressure such as the development of large stresses within the thin-walled torsional load cell.

Figure 7:
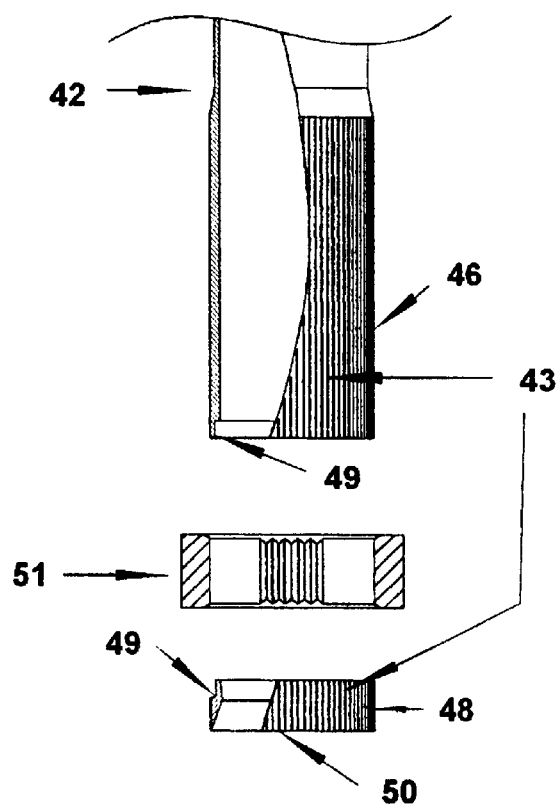
FIG. 7 is a broken away view of the lower portion of a probe cylinder.
Figure 8:
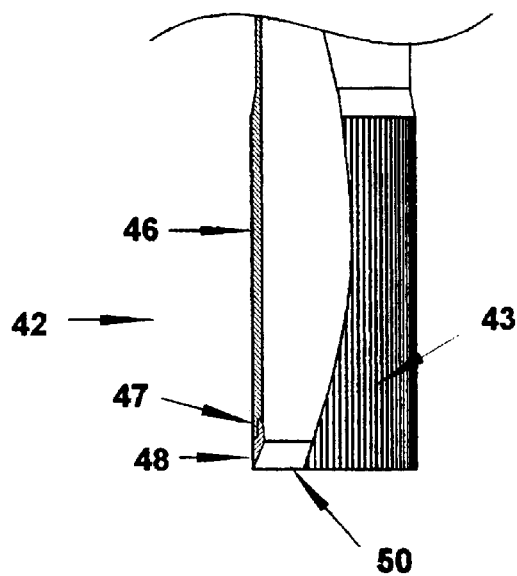
FIG. 8 is a broken away view of the lower portion of a probe cylinder.

As shown in FIGS. 7 and 8, the cylinder 42, having longitudinal grooves 43, may include an upper part 46 and a replaceable lower part 48 having a penetrating edge 50. During testing, the lower part 48 is attached to the upper part 46. An example of an effective method of attachment is to press the lower part 48 into the upper part 46. An alignment tool 51 is used to align the longitudinal grooves 43 of the lower part 48 with the grooves 43 of the upper part 46 during the pressing operation. The lower part 48 remains secure relative to the upper part 46 by machining the upper part 46 and the lower part 48 to provide a press fit 47. In the event that, in service, the penetrating edge 50 of the lower part 48 becomes excessively worn or damaged, it is simply pressed out of the upper part 46. A new lower part 48 is then pressed into the upper part restoring the cylinder to its original condition. Since a lower part is far less expensive than the entire cylinder and is easily replaced, the use of segmented cylinders is cost effective. The lower and upper parts may have mating offsets 49.

It may be possible to use various information that can be determined from the results of a single cylinder torsional cylindrical shear test to provide an indication of liquefaction resistance. For example, liquefaction resistance may be indicated by the maximum shear strains estimated to be developed within the tested soils during tests of a high level of excitation using the torsional cylindrical impulse shear test with a single open ended test cylinder. In the torsional cylindrical impulse shear test, shown schematically in FIG. 1, the testing element is a single open ended cylinder. The cylinder is excited by a torsional impulsive loading. The response is a rotary movement of the cylinder. The maximum shear strain developed in the tested soil can be effectively inferred from the quantities measured using this test. Highly liquefiable soils should show high maximum shear strains, soils that are resistant to liquefaction should show low maximum shear strains, and moderately liquefiable soils should show intermediate maximum shear strains. For higher levels of excitation, the torsional cylindrical impulse shear test has been found to induce the greatest maximum strains in saturated loose, silty sand deposits (likely, high liquefiable) and the least in clayey deposits (likely, nonliquefiable). The maximum shear strain is generally estimated analytically as part of the analytical simulations carried out to estimate shear moduli and related parameters. Estimates of maximum shear strains could also be obtained directly from measurements made during tests. Alternatively, in place of the maximum shear strain, an indication of liquefaction resistance may be obtained using the measured maximum porewater pressure developed in the test soil during a test.

The torsional cylindrical impulse shear test offers a unique combination of features. This combination is expected to result in particularly precise indications of in situ liquefaction resistance relative to those provided by other widely used in situ methods. First, the torsional cylindrical impulse shear test applies reasonably pure shear stresses to the test soil. Second, these stresses are of a reasonably high level. Third, the shear stresses result in reasonably pure shear strains. This combination of features is appealing from a fundamental standpoint. Liquefaction is believed to be caused mainly by shearing loads. These shearing loads are generally reasonably large, and among the most visible consequences are large shear strains. While the existing methods have important strengths, none has this combination of features that may be important for obtaining reasonably precise indications of in situ liquefaction resistance. For example, using low strain methods, effects of important high strain factors such as dilation may not be as fully reflected as when using the torsional cylindrical impulse shear test.

Figure 9:
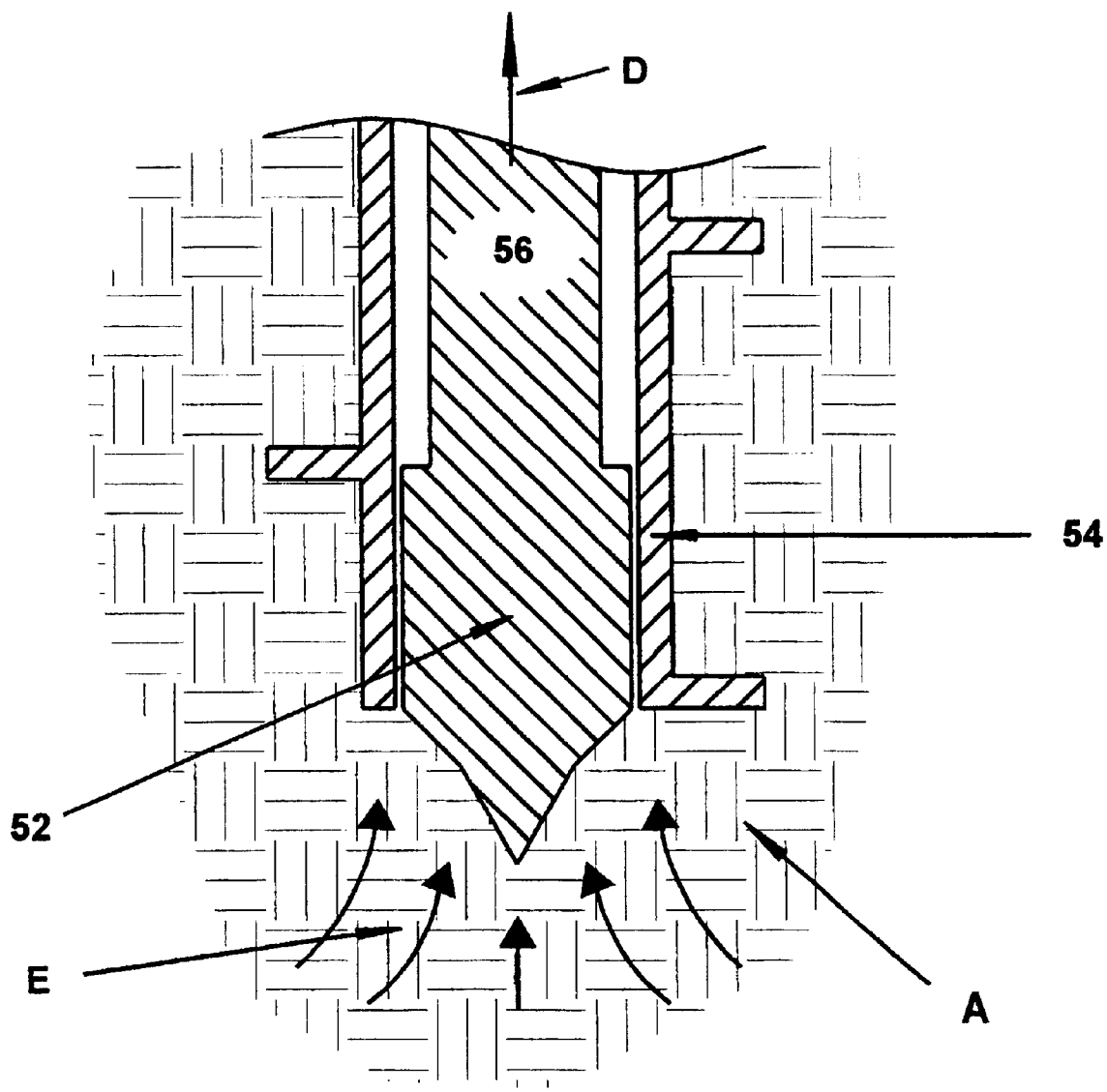
FIG. 9 is a cross-sectional view of a conventional auger plug.

Regarding FIG. 9, when drilling to a particular test depth, for sampling as well as testing operations, the lower end of the auger assembly 54 may be plugged to prevent the rise of soil below the auger assembly 54 toward or into the assembly. At the test depth if the soil has risen toward the auger, then this soil, which is test soil, will have been disturbed. The test results would not reflect the desired characteristics of the undisturbed soil. However, a conventional plug 52 may still allow the soil to rise toward the auger when the plug is removed in preparation for testing. The plug 52, which is essentially a solid cylinder, covers the inner bore of the auger. It is removed from the auger assembly 54 by raising the drill rod 56 to which the plug is attached. During the initial movement of the plug (indicated at "D"), suction may develop between the plug and the soil A below. The suction causes the soil below to follow the plug as indicated by the arrows "E" and thus, the test soil moves upwardly towards the auger and becomes disturbed.

Figure 10:
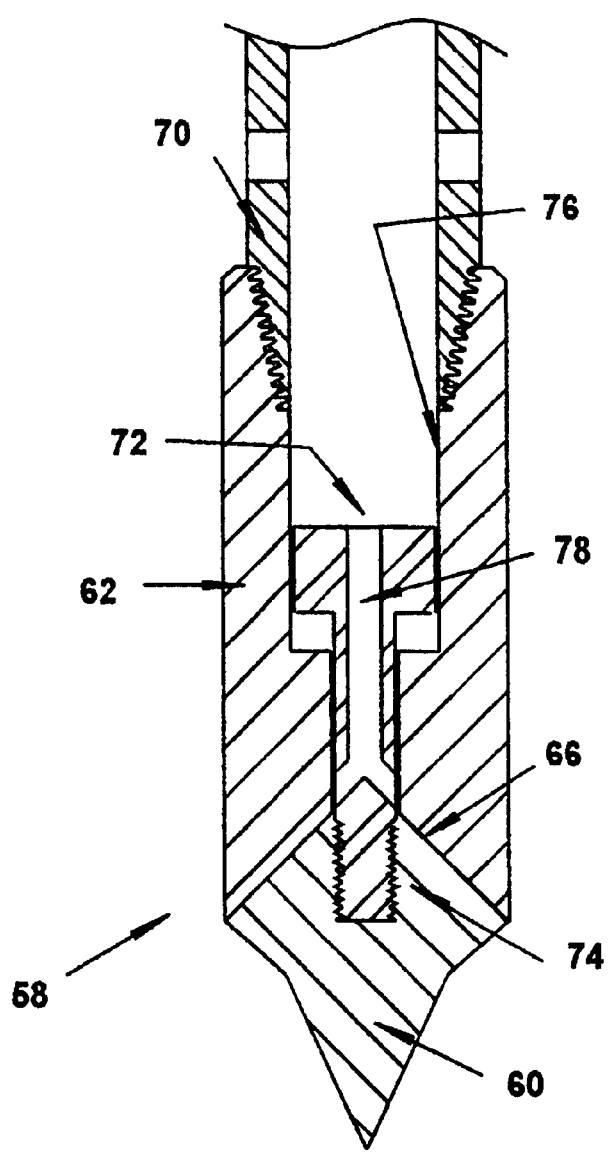
FIG. 10 is a cross-sectional view of an improved auger plug in a first position.

Referring now to FIG. 10, a special auger plug 58 attached to a modified drill rod 70 reduces the suction developed between the auger plug and the soil below during removal of the plug. The plug consists of two main components, a pilot bit/valve assembly 60 and a housing 62 that may be separated from each other by a fixed amount. During drilling, when the pilot bit/valve assembly 60 is closed by compression from the soil below as shown in FIG. 10, the two components are prevented from rotating relative to each other about the longitudinal axis by a locking wedge 66 and the plug acts conventionally.

The assembly 60 includes a T-shaped, hollow stem member 72 threaded to the end 74. The stem 72 is adapted for sliding movement within the bore 76. A passage 78 is defined through the stem 72. The facing surfaces of the assembly 60 and housing 62 are mating wedge shaped surfaces.

Figure 11:
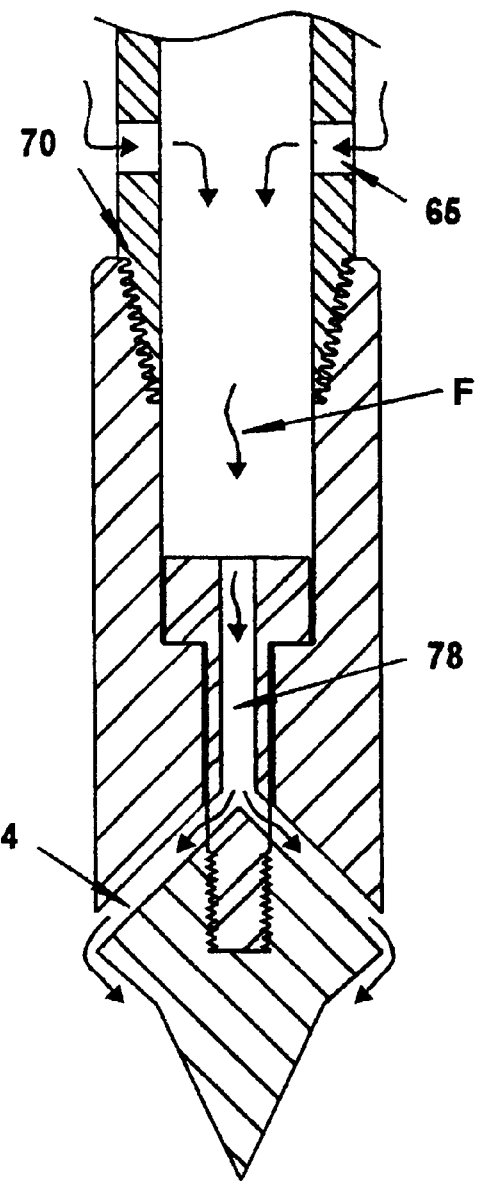
FIG. 11 is a cross-sectional view of the plug shown in FIG. 10 in a second position.

After the auger assembly has been drilled to the test depth, the plug 58 is removed. However, during the initial movement of the drill rod 70, only the upper portion of the plug is raised, as shown in FIG. 11. This causes the valve to open, allowing drilling fluid F, which is placed in the auger assembly above the plug to flow through fluid ports 65, through the opening 64, around the pilot bit/valve assembly 60, and into contact with the soil below the pilot bit/valve assembly 60. Thus, suction forces that act on the soil below conventional plugs as they are being removed are reduced. As a result, the tendency of the soil below the augers to rise upon the removal of the plug is reduced. By suppressing the rise of soil toward the augers during the removal of the plug from the augers, disturbances in the test soil should be minimized. As a result, single cylinder torsional cylindrical shear tests, for example, may reflect the characteristics of undisturbed soil more closely.

While the present invention has been described with respect to a limited number of embodiments, those skilled in the art will appreciate numerous modifications and variations therefrom. It is intended that the appended claims cover all such modifications and variations that fall within the true spirit and scope of the present invention.

What is claimed is:

1. A soil testing assembly comprising:

a soil testing cylinder;

a housing;

an extractor rod connecting said testing cylinder and said housing while allowing relative axial movement between the rod, the housing and the testing cylinder; and a torsional load cell, said rod extending through said torsional load cell.

2. The assembly of claim 1 wherein said rod has first and second enlarged ends.

3. The assembly of claim 1 including a member arranged to cause axial loading to bypass said cell.

4. The assembly of claim 1 including a torsional load cell and a first member, said cell being coupled to said first member, said first member adapted to allow said housing to axially engage said cylinder without axially loading said cell.

5. The assembly of claim 4 wherein said housing may be selectively disengaged from said cylinder such that rotary motion is conveyed from said first member to said cylinder through said load cell.

6. The assembly of claim 1 adapted to implement a single cylinder torsional cylindrical shear test.

7. A method for testing soil comprising:

rotating a test cylinder in a soil sample;

extending an extractor rod through a torsional load cell;

measuring torsional loading using said torsional load cell; and causing axial loads to bypass said load cell.

8. The method of claim 7 including, when said cylinder is being inserted into a soil sample, causing axial loading to bypass said cell.

9. The method of claim 7 including, when said cylinder is being withdrawn from a soil sample, causing axial loading to bypass said cell.

10. The method of claim 7 including implementing a torsional cylindrical shear test.

\* \* \* \* \*